United States Patent
Liu et al.

(10) Patent No.: US 8,969,309 B2
(45) Date of Patent: Mar. 3, 2015

(54) CRYSTAL OF PEPTIDE SUBSTANCE AS WELL AS THE PREPARATION METHOD AND USE THEREOF

(75) Inventors: Shidong Liu, Shanghai (CN); Zhaoli Zhang, Shanghai (CN); Zhonghao Zhuo, Shanghai (CN); Xiaoming Ji, Shanghai (CN); Xiaoliang Gao, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 90 days.

(21) Appl. No.: 13/811,367

(22) PCT Filed: Jul. 20, 2011

(86) PCT No.: PCT/CN2011/077382
§ 371 (c)(1),
(2), (4) Date: Jan. 21, 2013

(87) PCT Pub. No.: WO2012/010092
PCT Pub. Date: Jan. 26, 2012

(65) Prior Publication Data
US 2013/0123197 A1    May 16, 2013

(30) Foreign Application Priority Data
Jul. 20, 2010   (CN) .......................... 2010 1 0230751

(51) Int. Cl.
*A61K 38/12* (2006.01)
*C07K 7/56* (2006.01)
*A61K 38/00* (2006.01)

(52) U.S. Cl.
CPC . *C07K 7/56* (2013.01); *A61K 38/12* (2013.01); *A61K 38/00* (2013.01)
USPC ........................................................ 514/21.1

(58) Field of Classification Search
CPC ................................... C07K 7/56; A61K 38/12
See application file for complete search history.

(56) References Cited

U.S. PATENT DOCUMENTS

2009/0291996 A1    11/2009   Korodi et al.

FOREIGN PATENT DOCUMENTS

| CN | 101659693 A | 3/2010 |
|---|---|---|
| WO | 2008/048627 A1 | 4/2008 |
| WO | 2010/064219 A1 | 6/2010 |

OTHER PUBLICATIONS

Schwartz et al. "Pneumocandins from *Zalerion arboricola*" The Journal of Antibiotics, vol. 45, No. 12, pp. 1853-1866, Dec. 1992.

*Primary Examiner* — Christina Bradley
(74) *Attorney, Agent, or Firm* — McClure, Qualey & Rodack, LLP

(57) ABSTRACT

The present invention discloses a crystal of a peptide substance and the preparation method as well as the use thereof. Said crystal B possesses peaks at the following 2θ angles in the X-ray diffraction pattern (XRPD): 3.2±0.2°, 5.4±0.2°, 6.2±0.2°, and 9.3±0.2°.

12 Claims, 5 Drawing Sheets

CRYSTAL OF PEPTIDE SUBSTANCE AS WELL AS THE PREPARATION METHOD AND USE THEREOF

CROSS REFERENCE RELATED APPLICATIONS

This application is a national phase of PCT/CN2011/077382 filed Jul. 20, 2011, which claims priority to China Application Serial No. 201010230751.4, filed Jul. 20, 2010, both of which are entirely incorporated herein by reference.

TECHNICAL FIELD

The present invention relates to the crystal of a compound, particularly, to the crystal of a peptide substance as well as the preparation method and use thereof.

BACKGROUND

Recently, cyclopeptides having antifungal activities have been discovered in the fermentation liquid of certain fungi. Most of such cyclopeptides are cyclohexapeptides, generally called echinocandins, such as WF11899, and echinocandin. These cyclopeptides can be chemically modified to obtain semisynthetic antibiotics which can be used clinically.

The compound of formula I having the cyclohexapeptide structure is a natural product obtained by fermentation. The compound can be used as the raw material for synthesizing the compound of formula II. The preparation method of formula I can be found in the preparation methods disclosed in U.S. Pat. Nos. 5,202,309, 5,194,377 and 6,610,822.

The acetate of the compound according to formula II can be used as the peptide antibiotics for treating invasive aspergillosis, candidosis in esophagus, intra-abdominal abscess, pleurisy, abdominal infection caused by *Candida* spp, and the fever caused by unidentified pathogens in neutropenia patient. At present, the acetate of the compound according to formula II (caspofungin acetate, with the trade name "CANCIDAS") is sold in many countries as antifungal agent administrated intravenously.

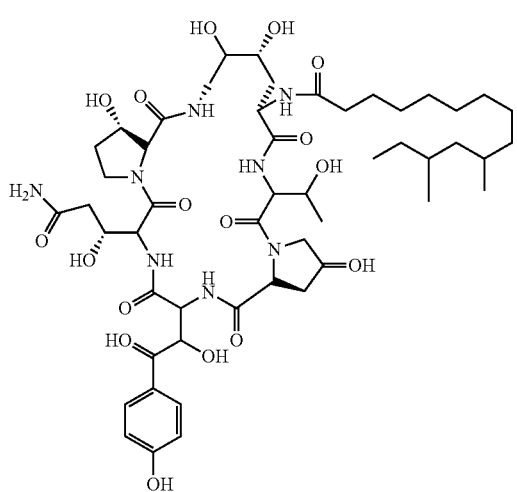

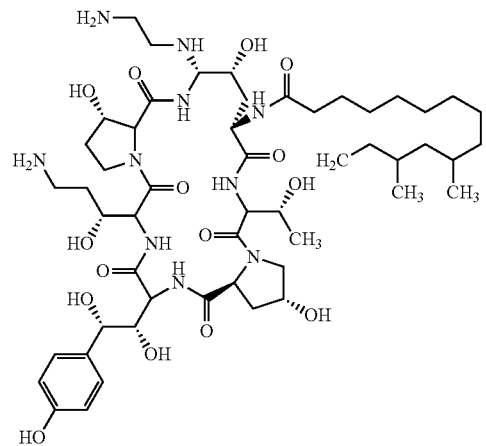

The compound of formula I is hard to crystallize, and generally, it is amorphous. For the end use of the compound according to formula I as a therapeutic or for the use thereof as the intermediates for the compound according to formula II, it is desirable to obtain crystals with high purity. U.S. Pat. No. 5,336,756 has disclosed a crystallization method using aqueous propanol as crystallizing solvent. Crystal A obtained by the method has peaks at the following 2θ angles in the X-ray diffraction pattern: 2.16±0.2°, 4.26±0.2°, 8.06±0.2°, 9.06±0.2°, 13.34±0.2°, 15.06±0.2°, 17.70±0.2°, 20.96±0.2°, 26.28±0.2°. It is concluded in U.S. Pat. No. 5,336,756 that except for n-propanol, other solvent is unsuitable for crystallization, but the method is time-consuming (12-20 hrs), low-yield (85.2% at the most), and unsuitable for industrial production.

Therefore, it is urgent to provide a method for preparing the crystal of the compound according to formula I and the crystal obtained, and said method should be readily and quickly conducted, and high-yielding.

SUMMARY OF THE INVENTION

The purpose of the invention is to provide a novel crystal of the compound according to formula I.

Another purpose of the invention is to provide the preparation method for the novel crystal.

Another purpose of the invention is to provide the use of the novel crystal.

In the first aspect of the invention, crystal B of the peptide substance according to formula I is provided, wherein, crystal B has peaks at the following 2θ angles in the X-ray diffraction pattern (XRPD): 3.2±0.2°, 5.4±0.2°, 6.2±0.2°, 9.3±0.2°;

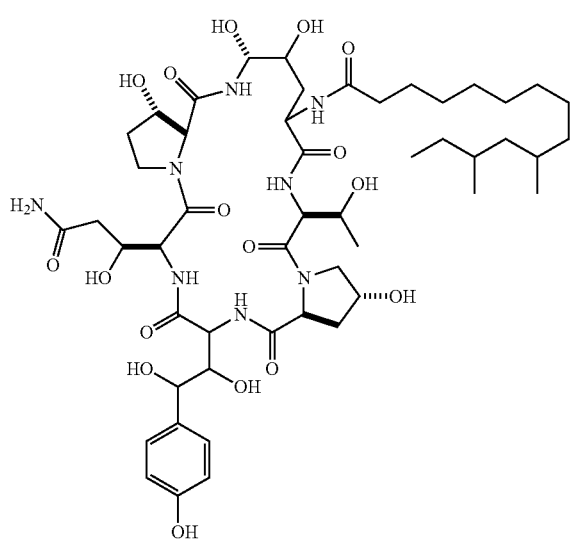

I

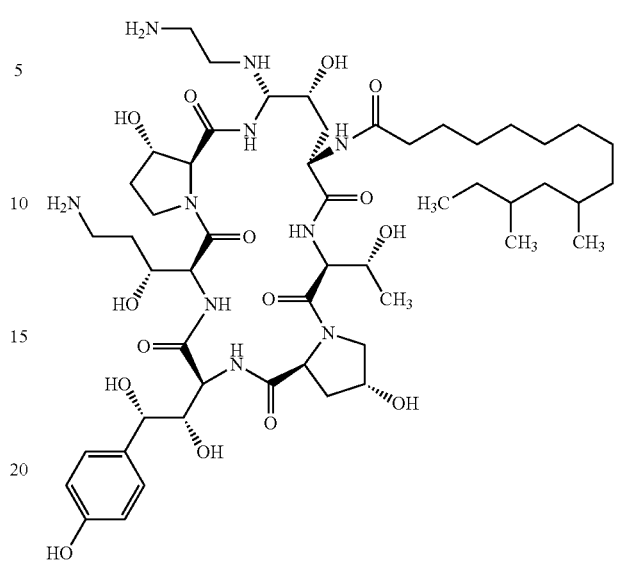

II

In another preferred example, crystal B has the maximum peak at 155-165° C. in the differential scanning calorimetry pattern (DSC).

In another preferred example, the infrared spectrum of crystal B is shown in FIG. 3.

In the second aspect of the invention, the preparation method of crystal B of the peptide substance provided by the invention is provided, wherein, said method includes the following steps:

(a) dissolving the compound of formula I in an aqueous organic solvent (i) to form solution a;

(b) obtaining crystal B of the peptide substance by reducing the temperature of solution a and/or adding another low polarity solvent (ii) into solution a.

In step (a), the temperature for dissolving the compound of formula I is 10° C.-80° C.; solution a comprises 20-250 mg/ml of the compound of formula I based on the total volume of solution a; the aqueous organic solvent (i) comprises 0.1-15 v/v % of water based on the total volume of the aqueous organic solvent (i); said organic solvent (i) is selected from one or more of the following group: $C_{1-4}$ alcohol and $C_{1-4}$ ketone; organic solvent (ii) is selected from one or more of the following group: $C_{3-7}$ ester, hexane, n-heptane, n-pentane, and dichloromethane.

In another preferred example, said organic solvent (i) is selected from one or more of the following group: methanol, ethanol, isobutanol, and acetone; organic solvent (ii) is selected from one or more of the following group: ethyl acetate, isopropyl acetate, hexane, n-heptane, n-pentane, and dichloromethane.

In another preferred example, the volume ratio of organic solvent (i) and organic solvent (ii) is 0.1-10:1.

In the above methods, said "reducing the temperature of solution a" means the temperature of the solution obtained in step (a) to 30-50° C.

In the third aspect of the invention, the use of the crystal of the peptide substance provided by the invention is provided, wherein, said crystal is used to prepare the compound of formula II.

One use of the crystal of the peptide substance provided by the invention is to prepare the medicaments for treating fungal infection.

In the fourth aspect of the invention, a pharmaceutical composition is provided, wherein said pharmaceutical composition comprises the crystal of the peptide substance provided by the invention and a pharmaceutically acceptable carrier.

In the fifth aspect of the invention, the preparation method according to the invention is provided, wherein, said method comprises the following steps:

mixing the crystal of the peptide substance provided by the invention and a pharmaceutically acceptable carrier to obtain the pharmaceutical composition of the invention.

Based on the above, a method for preparing the crystal of the compound according to formula I and the crystal obtained are provided by the invention, and said method is readily and quickly conducted, and high-yielding.

THE MODE FOR CARRYING OUT THE INVENTION

Figure 1:
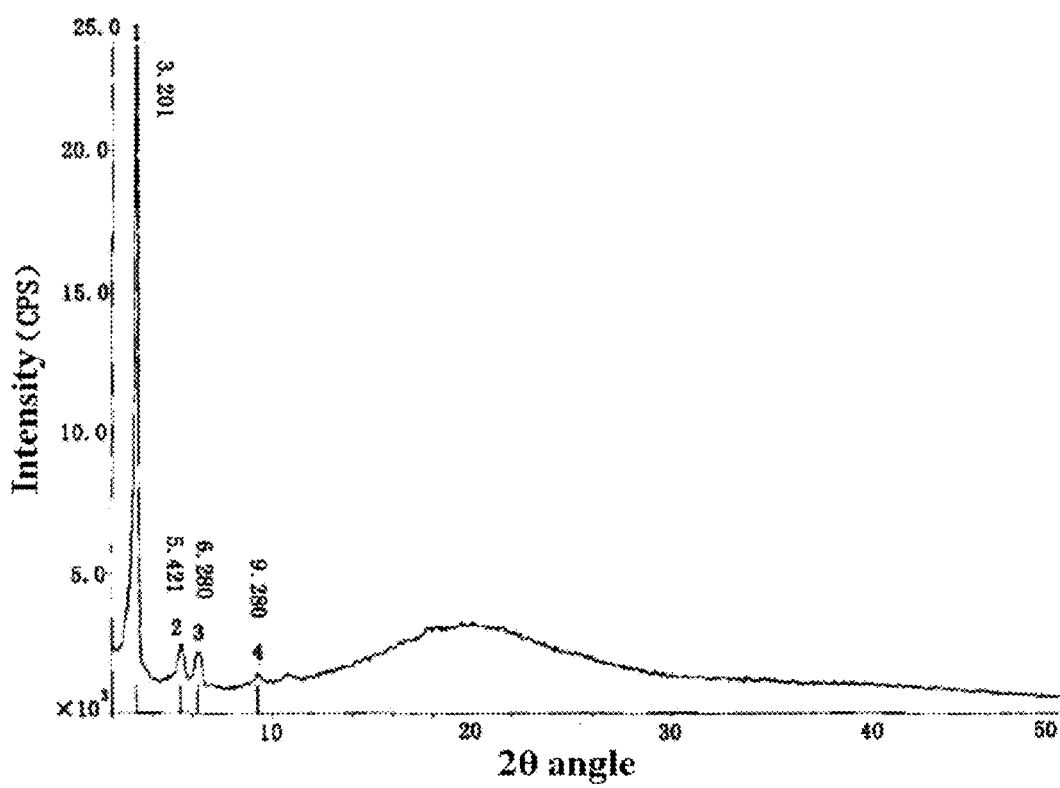
FIG. 1 is the X-ray powder diffraction pattern of crystal B of the compound according to formula I.

Upon research, the inventors have discovered that the compound of formula I can be dissolved at relative low temperature by using certain solvents, which in turn obtain the crystal with minor impurities, and the yield of the crystal is very high.

In the present invention, the compound of formula I was dissolved in the aqueous organic solvent (i), such as the aqueous methanol, ethanol, propanol, etc., and then the temperature of the resulted solution was reduced, alternatively, organic solvent (ii) (such as ethyl acetate, propyl acetate, etc.) was added while reducing the temperature of the resulted solution for promoting the precipitation of the crystal, thereby obtaining crystal B. In U.S. Pat. No. 5,336,756, it is believed that alkyl alcohol such as methanol, ethanol are not suitable for crystallization. However, the inventors have discovered that the crystals with minor impurities and good crystal form can be obtained by using such solvents, and the yield is very high.

The Preparation of Crystal B of the Compound According to Formula I

In the present invention, the term "crystal" means the solid of a molecule or atom complex showing specific arrangement.

During the research, the inventors have discovered that the compound of formula I can be dissolved in suitable solvents, and then another solvent can be used and/or the temperature can be reduced, thereby the compound of formula I can be precipitated from the solution.

Therefore, the preparation method for the crystal of the compound according to formula I is provided, said method comprising the following steps:

(a) dissolving the compound of formula I in the aqueous organic solvent (i) to form solution a;

(b) obtaining crystal B of the peptide substance by reducing the temperature of solution a and/or adding another low polarity solvent (ii) into solution a.

In one embodiment of the present invention, the crystal of the compound according to formula I was obtained by the following steps:

(a) dissolving the compound of formula I in the aqueous organic solvent (i) to form solution a;

(b) obtaining crystal B of the compound of formula I by reducing the temperature of solution a.

In another embodiment, in step (a), the temperature for dissolving the compound of formula I is 10° C.-80° C., preferably, 30° C.-60° C.

In another embodiment, solution a comprises 20-250 mg/ml of the compound of formula I based on the total volume of solution a in step (a), preferably, 50-200 mg/ml.

In another embodiment, said organic solvent (i) in step (a) is selected from one or more of the following group: $C_{1-4}$ alcohol, and $C_{1-4}$ ketone, preferably, one or more of the following group: methanol, ethanol, iso-butanol, and acetone.

In another embodiment, the aqueous organic solvent (i) in step (a) comprises 0.1-15 v/v % of water based on the total volume of the aqueous organic solvent (i), preferably, 1-12 v/v %, more preferably, 4-8 v/v % of water.

In another embodiment, in step (b), the temperature was reduced to 30-50° C., preferably, 30-10° C., more preferably, 25-10° C.

In another embodiment of the invention, the method for obtaining crystal B of the compound according to formula I includes the following steps after step (a):

(b') reducing the temperature of the solution, and adding solvent (ii) at the same time for precipitating crystal B of the compound according to formula I.

In another embodiment, said solvent (ii) in step (b') is selected from one or more of the following group: $C_{3-7}$ ester, hexane, n-heptane, n-pentane, and dichloromethane, preferably, selected from one or more of the following group: ethyl acetate, isopropyl acetate, hexane, n-heptane, n-pentane, and dichloromethane.

In another embodiment, in step (b'), the temperature was reduced to 30-50° C., preferably, 30-10° C., more preferably, 25-10° C.;

In another embodiment, in step (b'), the volume ratio of organic solvent (i) and organic solvent (ii) is 1-8, preferably 2-5, more preferably 3-4.

The purity for crystal B of the compound according to formula I prepared by the method according to the invention is high, therefore, it is preferred to be used to prepare the compound of formula II.

Identification of Crystal B of the Compound According to Formula I and the Properties Thereof After the crystal of the compound according to formula I was obtained, the inventors investigated the properties thereof by many methods and instruments.

"X-ray powder diffraction", also named as "X-ray polycrystal diffraction (XRPD)" is the routine experimental method used to detect the structure of a crystal (i.e., crystal form) at present. X-ray powder diffractometer is used to produce a serial of diffraction patterns when X-ray passing through a crystal. In the pattern, different diffraction curves and the intensities thereof depend on the atomic cluster with certain structure, thereby determining the crystal structure.

The method for obtaining the X-ray powder diffraction pattern of a crystal is known in the art. For example, the pattern can be obtained by using Bruker Model D8 Advanced X-ray powder diffractometer, wherein the scanning rate is 2°/min, and copper irradiated target is used.

Crystal B of the compound of formula I according to the invention possesses specific crystal form, and there are specific characteristic peaks in the XRPD pattern. Particularly, the crystal of the compound I according to the invention has peaks at the following 2θ angles in the X-ray diffraction pattern: 3.20±0.2°, 5.42±0.2°, 6.28±0.2°, 9.28±0.2°. Preferably, the crystal of the compound I according to the invention possesses the X-ray diffraction pattern substantially identical with FIG. 1.

"Differential scanning calorimetry" (DSC) is a technology for measuring the relationship of energy difference between the tested substance and the reference and temperature during the heating process. On the DSC pattern, the location, form and number of the peak are relevant to the properties of the substance, therefore, the substance can be qualitatively identified by DSC.

Said method is commonly used in the art to detect many parameters of a substance, such as the phase transition temperature, glass transition temperature and reaction heat.

When a substance is in a non-crystalline form, there will be no exact melting point during the heating process. The crystal of the compound of formula I according to the present invention possesses the exact melting point, that is, the crystal will be converted from the solid phase into the liquid phase in a narrow temperature range during the heating process.

DSC is known in the art. For example, DSC pattern of a crystal can be obtained by using DSC Q20 differential scanning calorimeter under the following conditions: warming rate of 10° C./min, from 25° C. to 200° C.

Figure 2:
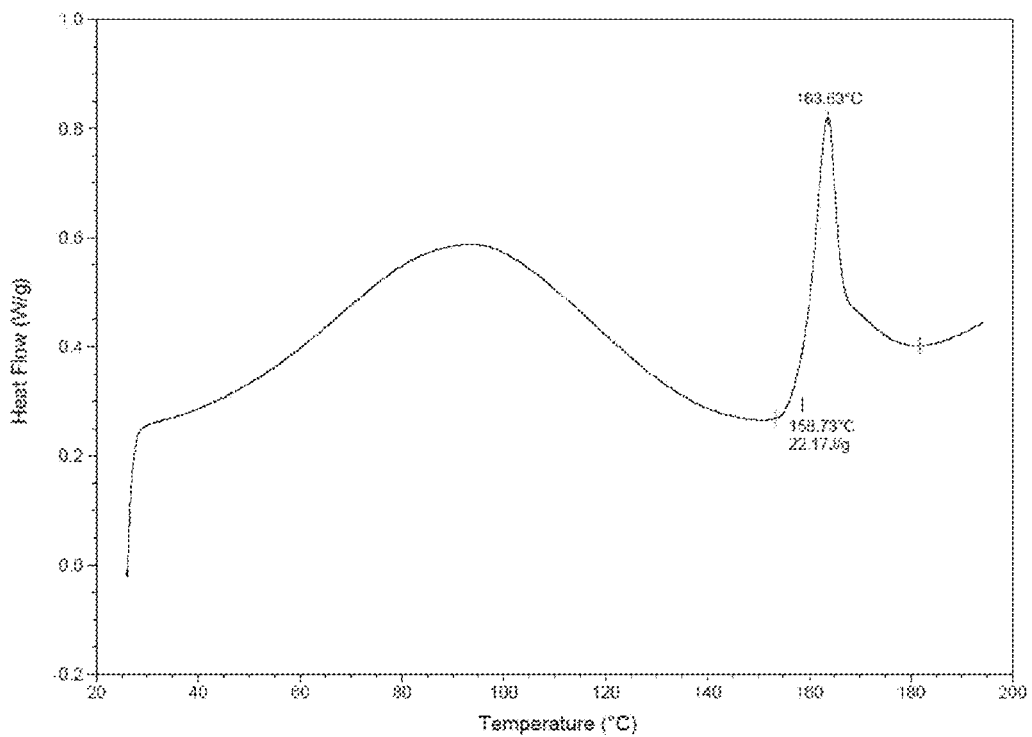
FIG. 2 is the differential scanning calorimetry (DSC) pattern of crystal B of the compound according to formula I.

In one embodiment of the present invention, crystal B of the compound according to formula I obtained by the method of the present invention was determined to have the maximum peak at about 155-165° C. by DSC. Preferably, crystal B of the compound of formula I according to the present invention possesses the DSC pattern substantially identical with FIG. 2. More preferably, the maximum peak can be found at 163.63° C.

The structure of a crystal can be determined by Infrared Spectrometry (IR) known in the art. For example, it can be determined by using PE Spectrum One B, tableting at KBr:sample=200:1, and scanning 400~4000 cm$^{-1}$. Crystal B of the compound of formula I according to the present invention has characteristic peaks at the following wave numbers: 3346.19 cm$^{-1}$, 2926.32 cm$^{-1}$, 2854.48 cm$^{-1}$, 2031.95 cm$^{-1}$, 1630.12 cm$^{-1}$, 1517.22 cm$^{-1}$, 1440.26 cm$^{-1}$, 1378.47 cm$^{-1}$, 1339.47 cm$^{-1}$, 1316.48 cm$^{-1}$, 1235.39 cm$^{-1}$, 1196.46 cm$^{-1}$, 1065.36 cm$^{-1}$, 968.65 cm$^{-1}$, 913.77 cm$^{-1}$, 839.57 cm$^{-1}$, 580.40 cm$^{-1}$, 551.40 cm$^{-1}$. Preferably, the crystal possesses the IR pattern substantially identical with FIG. 3.

Use of Crystal B of the Compound According to Formula I as Well as the Composition Comprising the Same In one aspect, a use of crystal B of the compound according to formula I has been provided in the present invention, wherein, said crystal can be used to prepare the compound of formula II.

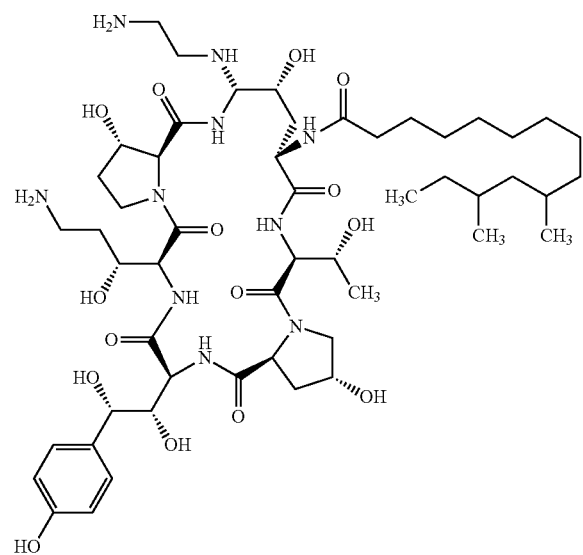

The synthetic routes for the compound of formula II have been disclosed in many patents (or applications), such as, WO 9747645, U.S. Pat. No. 5,552,521.

In another aspect, crystal B of the compound according to formula I provided in the present invention also can be used directly to prepare medicaments for treating fungal infection. The present invention further provides a pharmaceutical composition comprising crystal B of the compound of formula I and a pharmaceutically acceptable carrier.

As used herein, the term "pharmaceutically acceptable carrier" means the carriers that can be used to administrate therapeutics, including various excipients and diluents. The term means the drug carriers which themselves are not necessary active ingredients, and will not produce undue toxicity upon administration. Suitable carriers are generally known to the skilled in the art. Detailed review regarding the pharmaceutical acceptable excipient can be found in Remington's Pharmaceutical Sciences (Mack Pub. Co., N.J. 1991). Pharmaceutically acceptable excipients in a composition may include liquid, such as water, saline, glycol and ethanol. Additionally, auxiliary substances, such as disintegrating agents, wetting agents, emulsifying agents, pH buffering substances, etc., can be present in the carriers.

As used herein, "the compound of formula I" and "the compound according to formula I" can be used interchangeably, both of which mean a amorphous substance with the structure of formula I. The compound of formula I can be obtained by the routine method in the art, for example (but not limited to), the preparation method disclosed in U.S. Pat. No. 5,202,309; alternatively, the compound can be obtained commercially, such as from Merck Co.

The advantages of the invention mainly include:
1. The novel crystal form of the compound according to formula I has been obtained in the present invention.
2. The method for preparing the novel crystal form of the compound of formula I provided by the present invention will have high yield of crystal.
3. The method for preparing the novel crystal form of the compound of formula I provided by the present invention will introduce less impurities, thereby facilitating the downstream synthesis and improving the purity of the compound of formula II.
4. The purity of the crystal obtained by the method provided in the present invention is higher than that of the crystal obtained by the reported methods.

The invention will be further illustrated with reference to the following specific examples. It is to be understood that these examples are only intended to illustrate the invention, but not to limit the scope of the invention. For the experimental methods in the following examples without particular conditions, they are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

The purity was detected by high performance liquid chromatography (HPLC) method. HPLC method was performed according to the method reported in Journal of Industrial Microbiology & Biotechnology (2001), 26, 216-221; the normal phase HPLC is employed:

silica gel column: 4.6 mm*250 mm;

Mobile phase: ethyl acetate:methanol:water=84:9:7 (V/V/V);

Detection wavelength: 278 nm.

EXAMPLE 1

Figure 6:
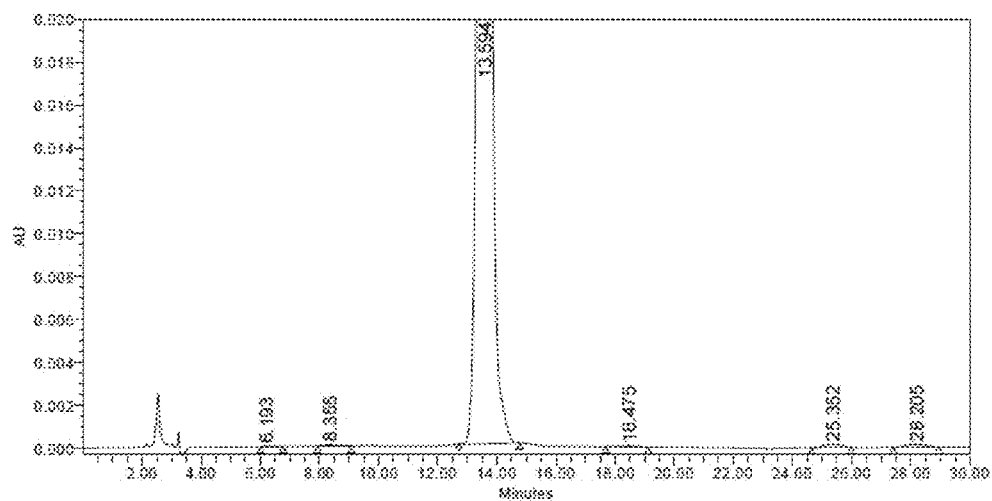
FIG. 6 is the HPLC pattern of the amorphous powder of the compound according to formula I.
Figure 7:
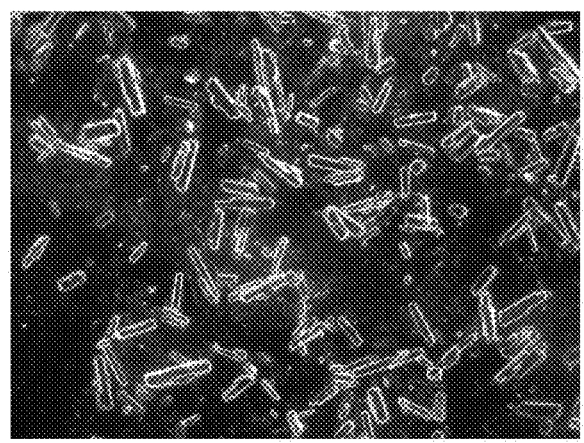
FIG. 7 is the microscopic image of crystal B of the compound according to formula I.
Figure 8:
FIG. 8 is the microscopic image of crystal A of the compound according to formula I.

Preparation of Compound I 146 g of solid powder of compound I was obtained according to the method disclosed in U.S. Pat. No. 5,202,309. The purity of the solid powder was determined as 96.1% by HPLC (see FIG. 6).

EXAMPLE 2

Preparation of Crystal B of the Compound of Formula I 8 g of compound I prepared in example 1 was dissolved in 38 ml of methanol at 40° C., 2 ml of water was added, and the resulted mixture was stirred for 1-2 hrs to dissolve compound I completely. The solution was cooled to 15° C., and crystal B of compound I was precipitated. 120 ml of isopropyl acetate was slowly added dropwise, the resulted mixture was stirred for 2 hrs at 15° C., filtered, and dried in vacuum to obtain 7.6 g of crystal B of compound I. The purity of the crystal was determined as 99.8% by HPLC. XRPD, DSC, IR patterns of the crystal can be found in FIGS. 1-3. HPLC pattern can be found in FIG. 4.

EXAMPLE 3

Preparation of Crystal B of Compound I 3.5 g of compound I prepared in example 1 was dissolved in 38 ml of ethanol at 45° C., 2 ml of water was added, and the resulted mixture was stirred for 1-2 hrs to dissolve compound I completely. The solution was cooled to −50° C., and crystal B of compound I was precipitated. 60 ml of isopropyl acetate was slowly added dropwise, the resulted mixture was stirred for 2 hrs at −50° C., filtered, and dried in vacuum to obtain 3.35 g of crystal B of compound I. The purity of the crystal was determined as 99.8% by HPLC. XRPD, DSC, IR patterns of the crystal can be found in FIGS. 1-3. HPLC pattern can be found in FIG. 4.

EXAMPLE 4

Preparation of Crystal B of the Compound of Formula I 2.5 g of compound I prepared in example 1 was dissolved in 48 ml of acetone at 40° C., 2 ml of water was added, and the resulted mixture was stirred for 1-2 hrs to dissolve compound I completely. The solution was cooled to 20° C., and crystal B of compound I was precipitated. 100 ml of ethyl acetate was slowly added dropwise, the resulted mixture was stirred for 2 hrs at 20° C., filtered, and dried in vacuum to obtain 3.35 g of crystal B of the compound of formula I. The purity of the crystal was determined as 99.8% by HPLC. XRPD, DSC, IR patterns of the crystal can be found in FIGS. 1-3. HPLC pattern can be found in FIG. 4.

EXAMPLE 5

Preparation of Crystal B of the Compound of Formula I 8 g of compound I prepared in example 1 was dissolved in 38 ml of methanol at 40° C., 2 ml of water was added, and the resulted mixture was stirred for 1-2 hrs to dissolve compound I completely. The solution was cooled to −50° C., and crystal B of compound I was precipitated. The crystal was filtered, and dried in vacuum to obtain 4.9 g of crystal B of the compound of formula I. The purity of the crystal was determined as 99.8% by HPLC. XRPD, DSC, IR patterns of the crystal can be found in FIGS. 1-3. HPLC pattern can be found in FIG. 4.

EXAMPLE 6

Preparation of Crystal B of the Compound of Formula I 8.4 g of compound I prepared in example 1 was dissolved in 99 ml of methanol at 40° C., 1 ml of water was added, and the resulted mixture was stirred for 1-2 hrs to dissolve compound I completely. The solution was cooled to 15° C., and crystal B of compound I was precipitated. 260 ml of isopropyl acetate was slowly added dropwise, the resulted mixture was stirred for 2 hrs at 15° C., filtered, and dried in vacuum to obtain 8.1 g of crystal B of the compound of formula I. The purity of the crystal was determined as 99.8% by HPLC. XRPD, DSC, IR patterns of the crystal can be found in FIGS. 1-3. HPLC pattern can be found in FIG. 4.

EXAMPLE 7

Preparation of Crystal B of the Compound of Formula I 9.6 g of compound I prepared in example 1 was dissolved in 44 ml of methanol at 40° C., 6 ml of water was added, and the resulted mixture was stirred for 1-2 hrs to dissolve compound I completely. The solution was cooled to 15° C., and crystal B of compound I was precipitated. 150 ml of isopropyl acetate was slowly added dropwise, the resulted mixture was stirred for 2 hrs at 15° C., filtered, and dried in vacuum to obtain 9.2 g of crystal B of the compound of formula I. The purity of the crystal was determined as 99.8% by HPLC. XRPD, DSC, IR patterns of the crystal can be found in FIGS. 1-3. HPLC pattern can be found in FIG. 4.

EXAMPLE 8

Purity and Stability Test

Crystal A of the compound of formula I was prepared as the comparative example (according to the solution disclosed in U.S. Pat. No. 5,336,756).

Figure 5:
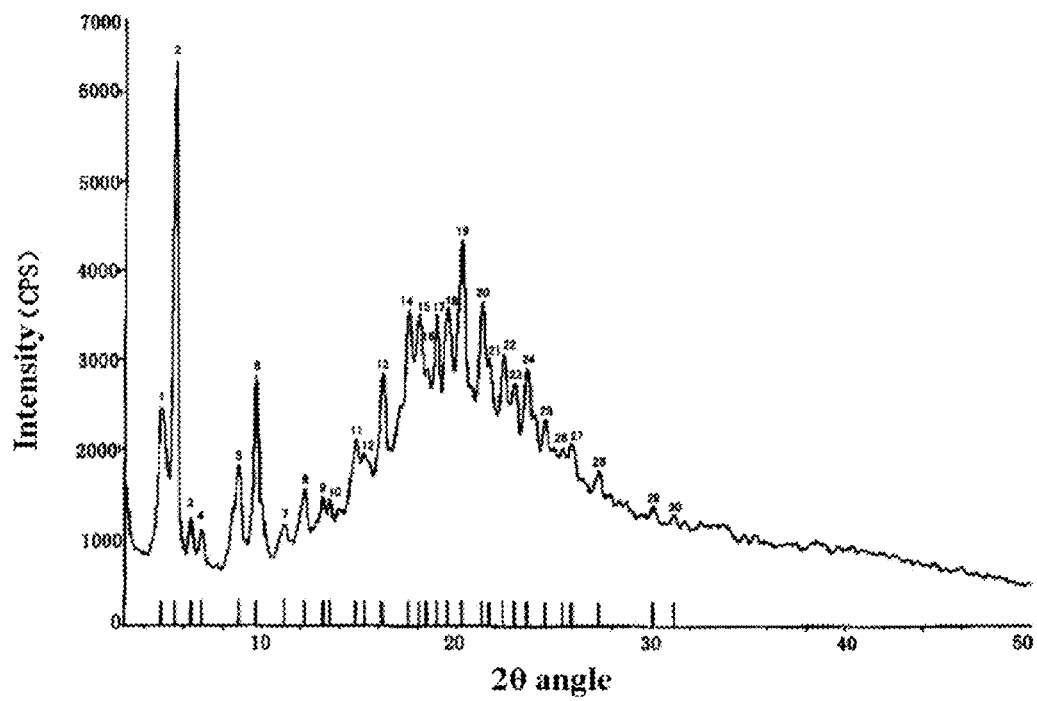
FIG. 5 is the X-ray powder diffraction pattern of crystal A of the compound according to formula I.

2.6 g of compound I prepared in example 1 was added into 250 ml round-bottom flask, 47.5 ml of n-propanol and 2.5 ml of water were added successively. The round-bottom flask was placed in water-bath at 60° C. with mixing to dissolve compound I completely. The flask was place at room temperature for 1-2 days, and the transparent rod-like crystal precipitated. The crystal was obtained upon filteration, and X-ray powder diffraction was performed (the diffraction pattern can be found in FIG. 5). The crystal has characteristic peaks at the following 2θ angles: 5.58±0.2°, 8.82±0.2°, 9.70±0.2°, 16.22±0.2°, 19.54±0.2°, 20.28±0.2°, 22.42±0.2°, and 23.62±0.2°. The concentration of the stock solution was determined as 20.77 g/l, and the yield of crystal was 58.4% (based on the pure compound). Two impurities can be found at retention time 25.352 and 28.205 min. The purity was reduced to 97.7%.

The purity and stability of samples prepared in the comparative example and examples 1-4 were compared. The method is described as follows:

The samples from comparative-example, example 1, example 2, example 3 and example 4 were obtained separately and kept at 25° C. for 14 days in sealed storage. And then the contents of the samples were tested by HPLC.

Results are listed in the following table:

| Sample | Experimental conditions | |
|---|---|---|
| | Content of the intial sample | Content of the sample stored at 25° C. for 14 days |
| Comparative example | 97.7 | 95.6 |
| Example 1 | 96.1 | 93.5 |
| Example 2 | 99.8 | 99.6 |
| Example 3 | 99.8 | 99.5 |
| Example 4 | 99.8 | 99.5 |

The results indicates that crystal B of the compound of formula I possesses better stability.

The above examples are merely the preferred examples for the present invention, and such examples cannot be used to limit the scope of the invention. The substantial technical contents according to the present invention are broadly defined in the claims. And any entities or methods accomplished by others should be considered as the equivalents and fall within the scope as defined by the claims, if said entities or methods are the same as those defined by the claims.

What is claimed is:

1. A method for preparing the Crystal B of the peptide substance of formula I, wherein crystal B has peaks at the following 2θ angles in the X-ray diffraction pattern (XRPD): 3.2±0.2°, 5.4±0.2°, 6.2±0.2°, 9.3±0.2°

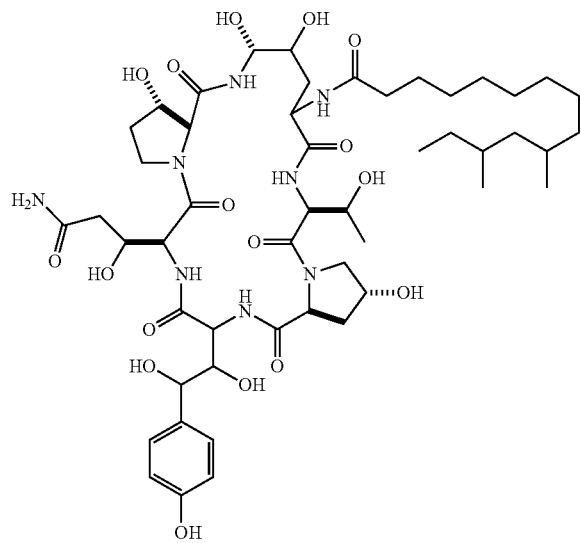

wherein, said method comprises the following steps:

(a) dissolving the compound of formula I in an aqueous organic solvent (i) to form solution a;

(b) obtaining crystal B of the peptide substance by reducing the temperature of solution a and/or adding another low polarity solvent (ii) into solution a;

wherein said organic solvent (i) is selected from one or more of the following group; methanol, ethanol, and acetone.

2. The method according to claim 1, wherein, in step (a), the temperature for dissolving the compound of formula I is 10° C.-80° C.

3. The method according to claim 1, wherein, in step (a), solution a comprises 20-250 mg/ml of the compound of formula I based on the total volume of solution a.

4. The method according to claim 3, wherein, the aqueous organic solvent (i) comprises 0.1-15 v/v % of water based on the total volume of the aqueous organic solvent (i).

5. The method according to claim 1, wherein said organic solvent (ii) is selected from one or more of the following group; $C_{3-7}$ ester, hexane, n-heptane, n-pentane, and dichloromethane.

6. The method according to claim 5, wherein said organic solvent (ii) is selected from one or more of the following group: ethyl acetate, isopropyl acetate, hexane, n-heptane, n-pentane, and dichloromethane.

7. The method according to claim 5, wherein, the volume ratio of organic solvent (i) and organic solvent (ii) is 0.1-10:1.

8. The method according to claim 1, wherein, said "reducing the temperature of solution a" means reducing the temperature of the solution obtained in step (a) to 30-50° C.

9. The method according to claim 2, wherein, in step (a), solution a comprises 20-250 mg/ml of the compound of formula I based on the total volume of solution a.

10. The method according to claim 9, wherein, the aqueous organic solvent (i) comprises 0.1-15 v/v % of water based on the total volume of the aqueous organic solvent (i).

11. The method according to claim 1, wherein crystal B possesses the maximum peak at 155-165° C. in the differential scanning calorimetry pattern (DSC).

Figure 3:
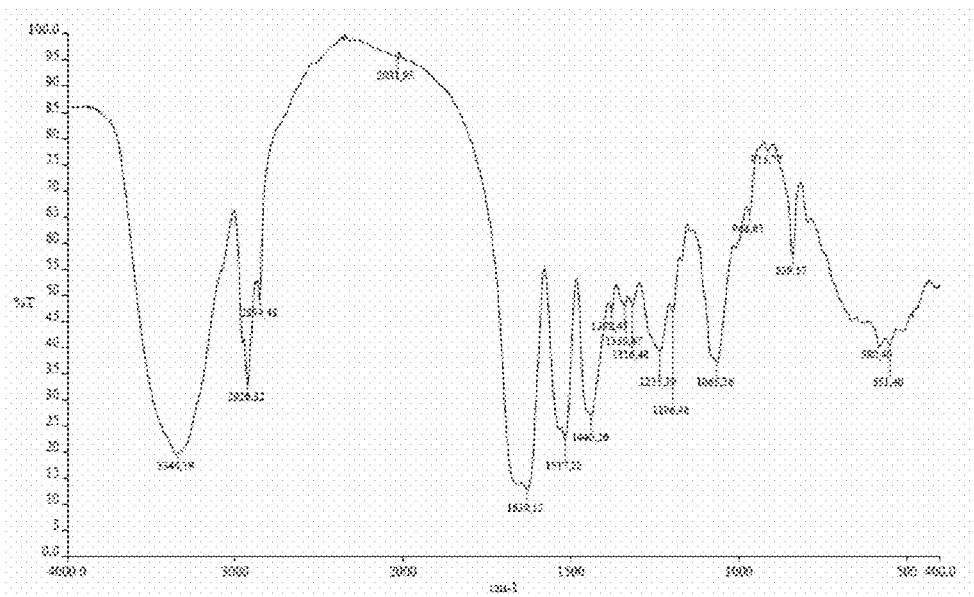
FIG. 3 is the infrared spectrum (IR) of crystal B of the compound according to formula I.
Figure 4:
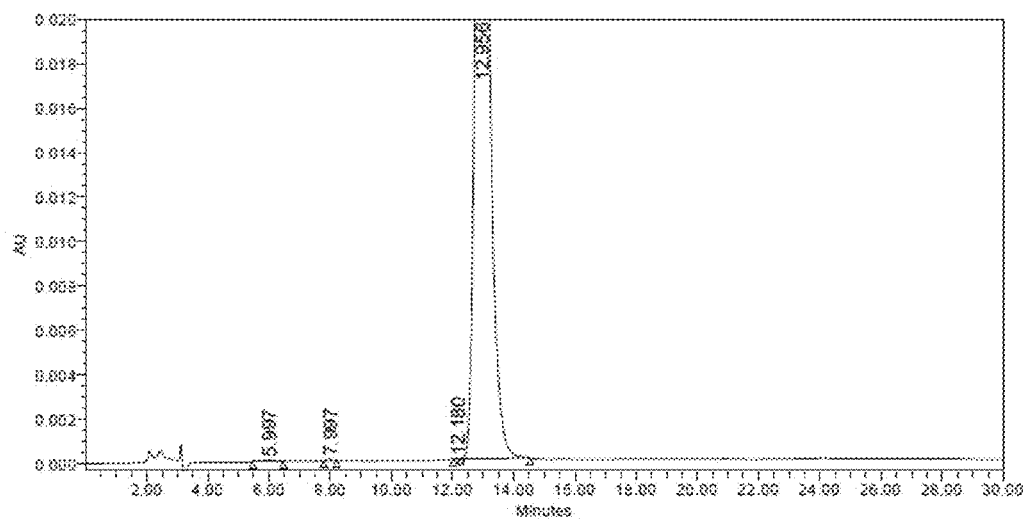
FIG. 4 is the HPLC pattern of crystal B of the compound according to formula I.

12. A method according to claim 1, wherein the infrared spectrum of crystal B is shown in FIG. 3.

* * * * *